US006991121B1

(12) United States Patent
Kipperman et al.

(10) Patent No.: US 6,991,121 B1
(45) Date of Patent: Jan. 31, 2006

(54) DISPOSABLE INFANT FORMULA FEEDING POUCH

(75) Inventors: Stuart R. Kipperman, Evansville, IN (US); Hagins Fugate, Newburgh, IN (US); George Nukuto, Des Plaines, IL (US)

(73) Assignee: Bristol-Myers Squibb Company, Princeton, NJ (US)

( * ) Notice: Subject to any disclaimer, the term of this patent is extended or adjusted under 35 U.S.C. 154(b) by 8 days.

(21) Appl. No.: 10/418,037

(22) Filed: Apr. 16, 2003

(51) Int. Cl.
*A61J 9/00* (2006.01)

(52) U.S. Cl. ...................... 215/11.1; 215/11.3; 220/9.1; 426/117

(58) Field of Classification Search ............... 215/11.1, 215/11.3, 11.6; 426/117; 222/92, 566; 220/9.1; 383/95, 96, 906
See application file for complete search history.

(56) References Cited

U.S. PATENT DOCUMENTS

| | | | | |
|---|---|---|---|---|
| 2,876,113 A * | 3/1959 | Barton | | 426/117 |
| 3,232,467 A * | 2/1966 | Barton | | 215/11.3 |
| 3,523,026 A * | 8/1970 | Emerson et al. | | 426/117 |
| 3,690,524 A * | 9/1972 | Haberhauer | | 222/573 |
| 4,637,934 A * | 1/1987 | White | | 426/117 |
| 4,678,092 A * | 7/1987 | Rane | | 215/11.3 |
| 4,718,778 A * | 1/1988 | Ichikawa | | 383/100 |
| 4,732,299 A * | 3/1988 | Hoyt | | 222/94 |
| 4,830,251 A * | 5/1989 | Conrad | | 215/10 |
| 5,257,865 A * | 11/1993 | Tani | | 388/78 |
| 5,511,697 A | 4/1996 | Gruenbacher et al. | | |
| 5,806,719 A | 9/1998 | Witty et al. | | |
| 5,823,383 A * | 10/1998 | Hins | | 220/601 |
| 6,000,848 A | 12/1999 | Massioui | | |
| 6,105,821 A | 8/2000 | Christine et al. | | |
| 6,142,344 A | 11/2000 | Kai | | 222/183 |
| 6,241,122 B1 * | 6/2001 | Araki et al. | | 222/92 |
| 6,241,132 B1 | 6/2001 | Morrison | | |
| 6,250,506 B1 | 6/2001 | Geiger et al. | | |
| 6,273,307 B1 | 8/2001 | Gross et al. | | |
| 6,439,429 B1 | 8/2002 | Gross | | |
| 6,612,428 B1 * | 9/2003 | Segovia et al. | | 206/219 |

FOREIGN PATENT DOCUMENTS

| | | |
|---|---|---|
| WO | WO85/04574 * | 10/1985 |
| WO | WO 85/04636 | 10/1985 |
| WO | WO 01/15653 A1 | 3/2001 |
| WO | WO 03/068631 A2 | 8/2003 |

* cited by examiner

*Primary Examiner*—Sue A. Weaver
(74) *Attorney, Agent, or Firm*—Nelson Mullins Riley & Scarborough

(57) ABSTRACT

An infant feeding pouch is provided which has collapsible walls mounted to a structural supporting fitment. A nipple for feeding an infant may be attached to the fitment.

31 Claims, 5 Drawing Sheets

DISPOSABLE INFANT FORMULA FEEDING POUCH

FIELD OF THE INVENTION

The present invention relates to disposable containers and, in particular, to a disposable infant formula feeding pouch.

BACKGROUND OF THE INVENTION

Infant feeding bottles have typically been formed from a relatively rigid plastic material that allows a caregiver or child to grip the bottle. The rigid nature of these bottles is advantageous for gripability. However, rigid bottles are also disadvantageous because they are relatively expensive to manufacture, require repeated washing and sterilization after each use and are bulky since they are not easily compressible.

Collapsible pouches, on the other hand, are cheaper to manufacture since they are formed from minimal amounts of materials. Disposable pouches also eliminate the need to wash and sterilize the bottles after each use since they are disposable. Moreover, because disposable pouches can be prepackaged with formula, either in liquid or dry form, the correct amount of formula can be administered during each feeding.

SUMMARY OF THE INVENTION

The present invention recognizes and addresses considerations of prior art constructions and methods and provides an infant feeding bottle including a flexible pouch and a fitment. The pouch includes a first wall, a second wall, and a base connected between the first and the second pouch walls, so that the first and the second pouch wall form an open end opposite the base. The fitment includes a body for supporting an inside edge of the first and the second pouch walls, a first vertical wall connected to the body and extending parallel to a central axis of the body, and a second vertical wall connected to the body and extending parallel to the first vertical wall and the central body axis. The fitment may further include a threaded opening for receiving a nipple or other feeding mechanism. The open end of the pouch receives the fitment body so that the first and second fitment walls are received within the pouch proximate the pouch walls.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
FIG. 1 is a perspective view of an infant feeding pouch of the present invention.

Repeat use of reference characters in the present specification and drawings is intended to represent same or analogous features or elements of the invention.

DETAILED DESCRIPTION OF THE PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

With reference now to the drawings, and in particular to FIGS. 1 to 3A, an embodiment of the new and improved infant feeding bottle designated generally by the reference numeral 10 will be described. Bottle 10 includes a collapsible pouch 12 and a fitment 14.

Collapsible pouch 12, which may be of special or conventional design, may be made from a flexible, heat-sealable polymeric sheet so as to have a first wall 16 and a second wall 18. Walls 16 and 18 may be formed from any suitable flexible material, and in one embodiment, FIG. 2A, may be formed from a suitable multi-layer FDA approved material for packaging food products. For example, referring to FIG. 2B, a suitable multi-layer material includes a first layer of aluminum oxide-coated polyester PET 15, a second layer of nylon 17, and a third layer of cast polypropylene 19. It should be understood that other materials may be used in place of each of the layers. For example, silica oxide-coated PET or foil may be utilized for one of the layers. A polypropylene layer will typically, but not always, form the inner surface of the walls since it may be used to heat bond the pouch to the fitment. The PET and nylon layers are interchangeable and either can be used to form the intermediate or outside layers if desired. The wall material may include oxygen and water barriers and, optionally, UV barriers. In one embodiment, the aluminum oxide layer provides an oxygen barrier.

Wall portions 16 and 18 may be sealable to each other at their edge portions, thereby defining an interior chamber 20. Chamber 20 is closed at a first end 22 by a base 23 and open at a second end 24 to form a mouth or opening into interior chamber 20. Base 23 may be even with the first end 22 of walls 16 and 18 (FIGS. 3 and 3A) or it may be recessed from first end 22 (not shown). That is, a gusset wall would create base 23 so that the pouch is free standing. Second end 24 is adapted to receive fitment 14 which, when bonded to walls 16 and 18, is securely attached to pouch 12.

Figure 3:
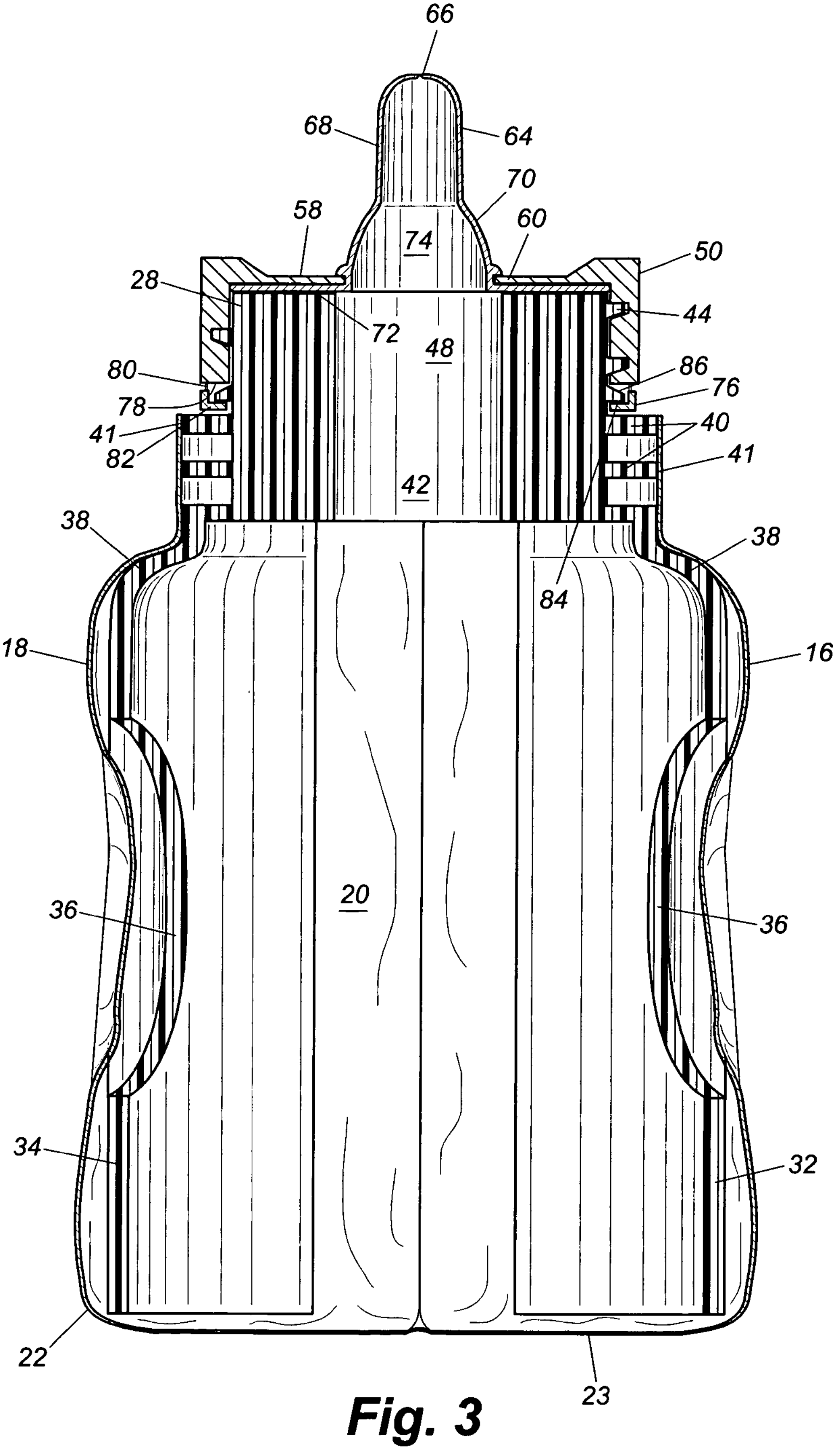
FIG. 3 is a sectional view of the infant feeding pouch of FIG. 1.
Figure 3A:
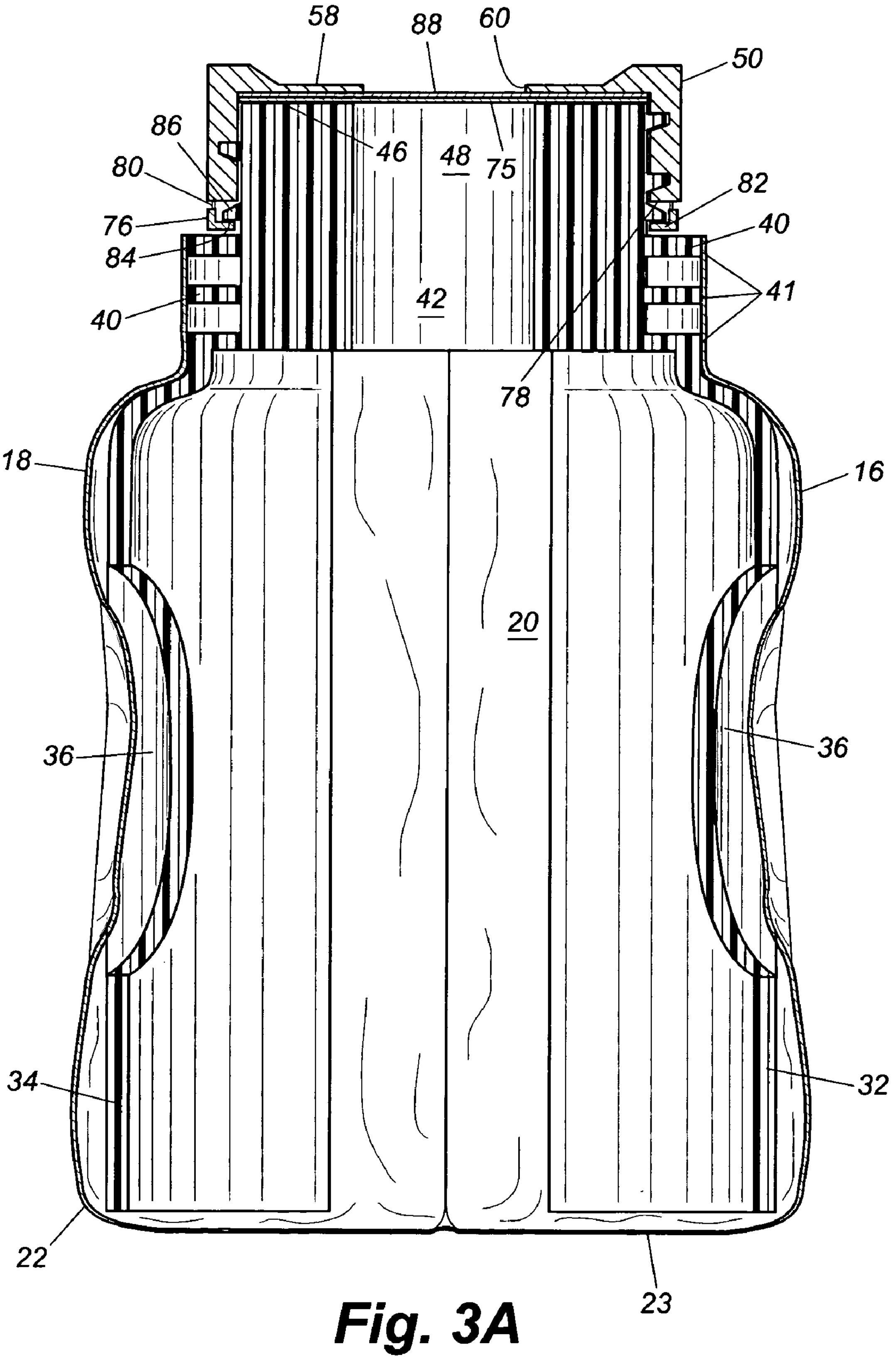
FIG. 3A is a sectional view of an embodiment of the infant feeding pouch of FIG. 1.

Fitment 14 contains two components: a fitment body 26 and a threaded cylindrical top portion 28. Cylindrical top portion 28 may be separately molded and attached to body 26, but in one embodiment, the two parts are integrally molded together. Body 26 and cylindrical top portion 28 may be molded from a polymeric material suitable for forming the fitment, as shown in FIGS. 3 and 3A. Suitable polymeric materials include, but are not limited to, polypropylene, polystyrene, polystyrene-acrylonitile, acrylonitile-butadiene-styrene, styrene-maleicanhydride, polycarbonate, polyethylene terephthalate, polyvinylcyclohexane, and blends thereof.

Fitment body 26 contains a bonding portion 30 and an axially downward extending structure. In one embodiment, the axially downward extending structure comprises two parallel fitment walls 32 and 34. Fitment walls 32 and 34 are generally rectangular, have a convex bow shape, and are sized substantially equal to the width of walls 16 and 18. Fitment walls 32 and 34 may be of any suitable spacing from each other but, in one embodiment, fitment walls 32 and 24 are adequately spaced apart so that they are proximate to the inside surface of walls 16 and 18. An inwardly extending shoulder portion 38 connects fitment walls 32 and 34 to bonding portion 30. Each wall may contain a recessed oval area 36 (FIGS. 3 and 3A) to enhance the caregiver's grip on pouch 12. Recess 36 may be round, rectangular, or any other shape to provide a gripping area to receive the caregiver's fingers.

When fluid is placed in the pouch, the pouch walls become relatively rigid under the pressure of the fluid. Without the fitment walls, the pouch would loose rigidity and become unstable and limp as the fluid is removed from the pouch during the feeding process. The loss of rigidity would cause the pouch to flop around in the caregiver's hand. Accordingly, the axially downward extending structure of fitment 14 supports the pouch so that it may stand upright and provide a rigid surface to enhance the pouch's gripability. The fitment walls also reduce the likelihood that product is squeezed out of the pouch under the gripping force of the caregiver and provide greater stability when the pouch collapses as the fluid is drained. Therefore, fitment walls 32 and 34 should generally be of sufficient thickness to enhance gripability and provide structural stability. In one embodiment, fitment walls 32 and 34 are in the range of about 0.5 mm to 1.5 mm thick but the wall thickness may vary depending on the application of the pouch and fitment and its intended contents.

Figure 2:
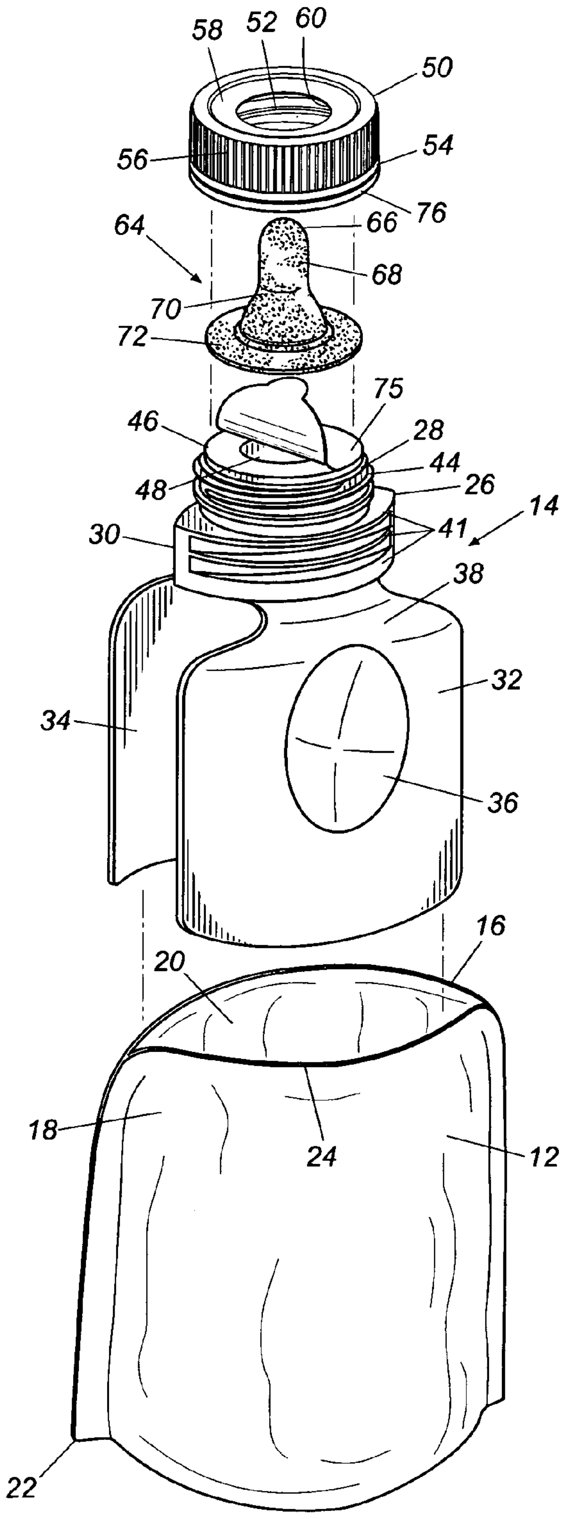
FIG. 2 is an exploded perspective view of the infant feeding pouch of FIG. 1.
Figure 2A:
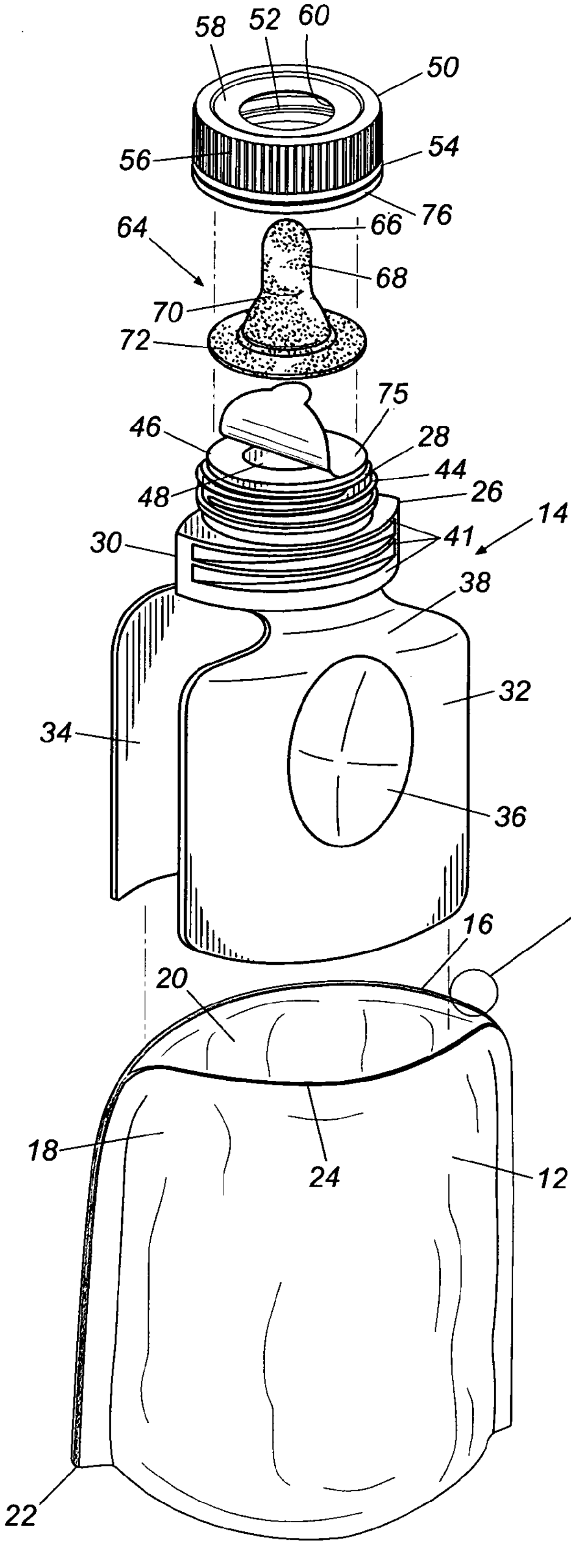
FIG. 2A is an exploded perspective view of another embodiment of the infant feeding pouch.
Figure 2B:
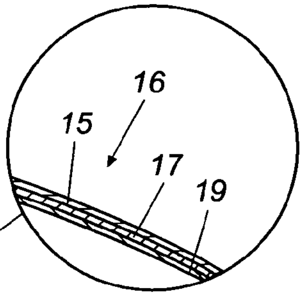
FIG. 2B is a sectional view of the pouch of FIG. 2A.

Referring to FIGS. 2 to 3A, bonding portion 30 is generally canoe shaped in cross section and contains a plurality of ribs 40. Each rib 40 defines a bonding surface 41 for bonding the fitment to the interior surface walls 16 and 18 proximate second end 24. Bonding portion 30 contains a central passageway or opening 42 that is in fluid communication with both an opening 48 defined in the cylindrical top portion 28 and the interior chamber 20. Openings 48 and 42 are of a restricted size to regulate the amount of product that flows from the interior chamber 20 of pouch 12 into and through nipple 64, especially when the caregiver squeezes the pouch. It should be understood that bonding portion 30 might not include ribs 40, but instead may contain flat, continuous, walls (not shown) for receiving the interior portion of the pouch walls 16 and 18.

Cylindrical top portion 28 contains a thread 44 about its outer periphery and a rim 46 that defines opening 48. Thread 44 is adapted to receive an annular cap 50 having a helical thread 52 on its inner circumference for removably securing cap 50 to the threaded cylindrical top portion 28. Outer circumference 54 of cap 50 may contain ribs or knurling 56 that allow the caregiver to more easily grasp cap 50 when removing it from or fitting it on cylindrical top portion 28. In addition to its internally threaded cylindrical wall, cap 50 includes an annular end wall 58, which defines an interior peripheral rim 60 dimensioned to fit around a portion of a nipple 64. Nipple 64 and cap 50 can thus be press fit together.

Referring to FIGS. 2 and 3, nipple 64 has a very shallowly curved surface 66 at the end of a mouthpiece 68. Nipple 64 widens out to a frustoconical section 70 located intermediate an annular flange 72 and mouthpiece 68. Annular flange 72 is dimensioned to seat on rim 46 of cylindrical top portion 28, and it defines a central aperture 74 therethrough, which is in fluid communication with opening 48, opening 42, and interior chamber 20. Aperture 74, defined by annular flange 72, allows fluid to flow from pouch 12 into and through nipple 64. A soft pliable material such as conventional rubber or silicone rubber may be used to form nipple 64, and nipple 64 may be of a standard size that is well known to those skilled in the art.

As shown in FIG. 3, nipple 64 is press fit into cap 50 so peripheral rim 60 surrounds nipple 64. Thus, mouthpiece 68 and frustoconical portion 70 extend upward through cap 50 so that the annular flange 72 engages a rearward surface of end wall 58. In this configuration, an outermost edge portion of the annular flange 72 is in abutting contact with the inner circumference of cap 50. Thus, threadably securing cap 50 onto top portion 28 causes the rearward surface of end wall 58 to compress nipple flange 72 against rim 46 to form a liquid-tight seal.

A releasable seal 75 (FIGS. 2 and 3A) attached to rim 46 allows for pouch 12 to be hermetically sealed, for example by vacuum packaging or by nitrogen flushing, either of which improves the product's stability. One skilled in the art of baby formula or food packaging will be familiar with such releasably attached seals for hermetic sealing. Specifically, adhesive or heat attaches a seal formed of polyvinyl chloride, polystyrene, or other suitable material to rim 46 to form an airtight seal during packaging. Therefore, cap 50 will not disturb the vacuum seal unless seal 75 is cut or removed. Seal 75 also provides a device to detect tampering with the packaged product. Other sealing means are possible, such as a breakaway plastic cover ultra-sonically welded to rim 46.

In addition to the releasably attached seal 75, bottle 10 may also include an anti-tamper ring 76 (FIGS. 3 and 3A). Anti-tamper ring 76 connects to a lower edge 78 of cap 50 by a plurality of relatively thin and frangible breakaway tongues or webs 80. Internally, radially inwardly projecting and angularly extending ridges 82 are formed on an inner circumference of anti-tamper ring 76, which engage an under surface 84 of a radially outwardly projecting flange 86 formed on cylindrical top portion 28. Thus, tensile forces rotationally fix anti-tamper ring 76 to flange 86, as cap 50 is unthreaded off bottle 10. As cap 50 is rotationally removed, both tensile and torsional forces acting on webs 80 cause the webs to sever allowing cap 50 to be completely removed and to indicate that the pouch contents have been exposed.

In another embodiment (FIG. 3A), cap 50 does not include nipple 64 press fit into cap 50 as described above. Instead, a substantially flat circular disc 88 located proximate the under surface of end wall 58 forms a seal when cap 50 is removably secured to threaded cylindrical top portion 28. Disc 88 should have an outer radius substantially equal to an inner radius of cap 50. Therefore, during packaging, as cap 50 is tightened on cylindrical top portion 28, rim 46 and the bottom surface of end wall 58 compress the disc to establish a seal. Disc 88 may comprise an aluminum annular shaped material bonded to a compressible annular shaped material formed, for example, from conventional rubber, silicone rubber, or other suitable compositions. Use of the compressible disc eliminates the need for a separate removable vacuum seal. However, bottle 10 can be packaged using an independent safety seal 75 and/or anti-tampering ring 76 in addition to compressible disc 88.

Pouch 12 attaches to bonding surface 41 of ribs 40, for example, by adhesive bonding, ultrasonic bonding, heat bonding, or by other suitable bonding means. When pouch 12 is bonded to fitment 14, fitment walls 32 and 34 engage the inner surface of pouch walls 16 and 18, respectively. Thus, when the caregiver grasps pouch 12, fitment walls 32 and 34 exert an outward force against the caregiver's grasp that prevents the pouch from collapsing under the gripping force.

Figure 4:
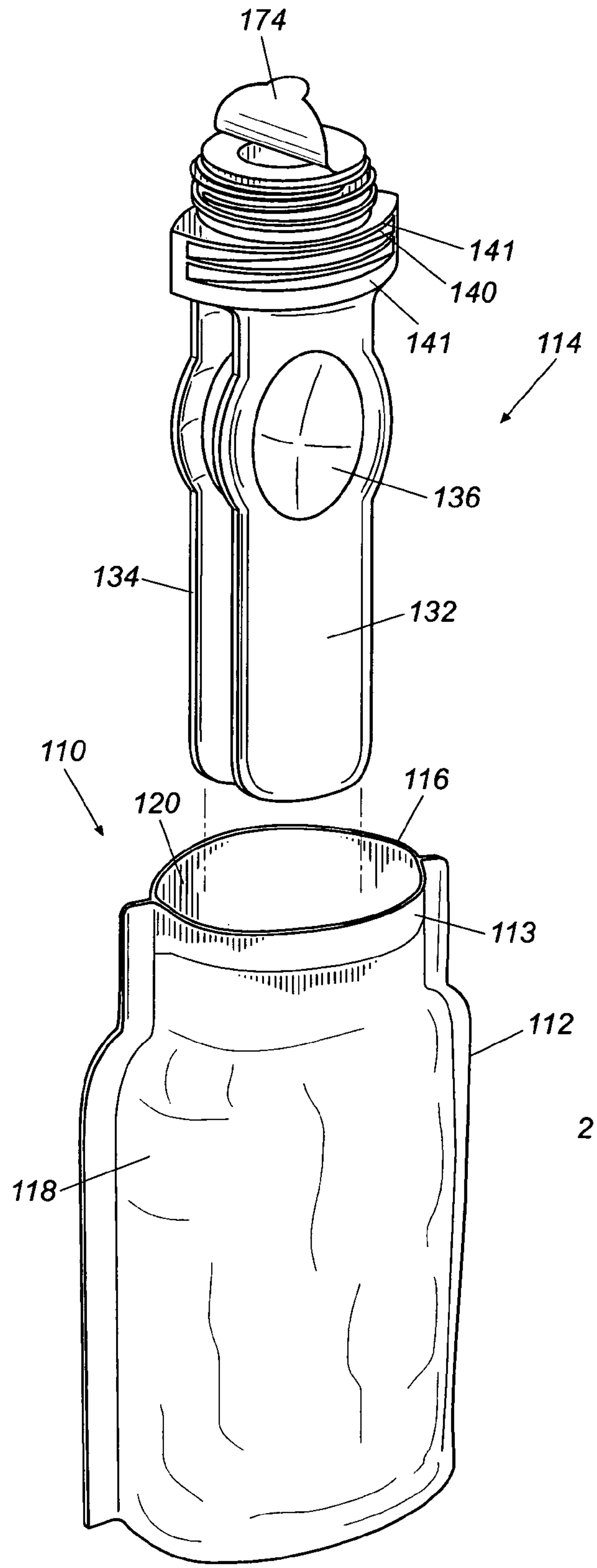
FIG. 4 is an exploded perspective view of an embodiment of an infant feeding pouch of the present invention.

FIG. 4 discloses another embodiment where a bottle 110 includes a pouch 112 adapted to receive a fitment 114. Pouch 112 and fitment 114 are formed substantially the same as pouch 12 and fitment 14 above. As in pouch 12, pouch walls 116 and 118 may be sealable to each other at their edge portions, thereby defining an interior chamber 120. Pouch 112 differs from pouch 12 in that it is narrower and contains a neck area 113. Neck 113 bonds to a bonding face 141 of ribs 140 to form a liquid and airtight seal. Fitment 114 differs from the embodiment shown in FIGS. 1–3 in that the downwardly extending axial structure includes fitment walls 132 and 134 that are substantially narrower than pouch walls 116 and 118. Fitment walls 132 and 134 connect to bonding faces 141 by heat bonding, sonic bonding, adhesive bonding, or the like and, when inserted into pouch 112, provide a support area for the caregiver to grip bottle 110 when feeding an infant. A recess 136, formed in walls 132 and 134, enhances the caregiver's grasp on bottle 110 by receiving the caregiver's thumb and forefinger. Similar to bottle 10, a seal 174 may be received on the fitment mouth. Otherwise, all other parts of bottle 110 are, and operate, substantially the same as in bottle 10.

Figure 5:
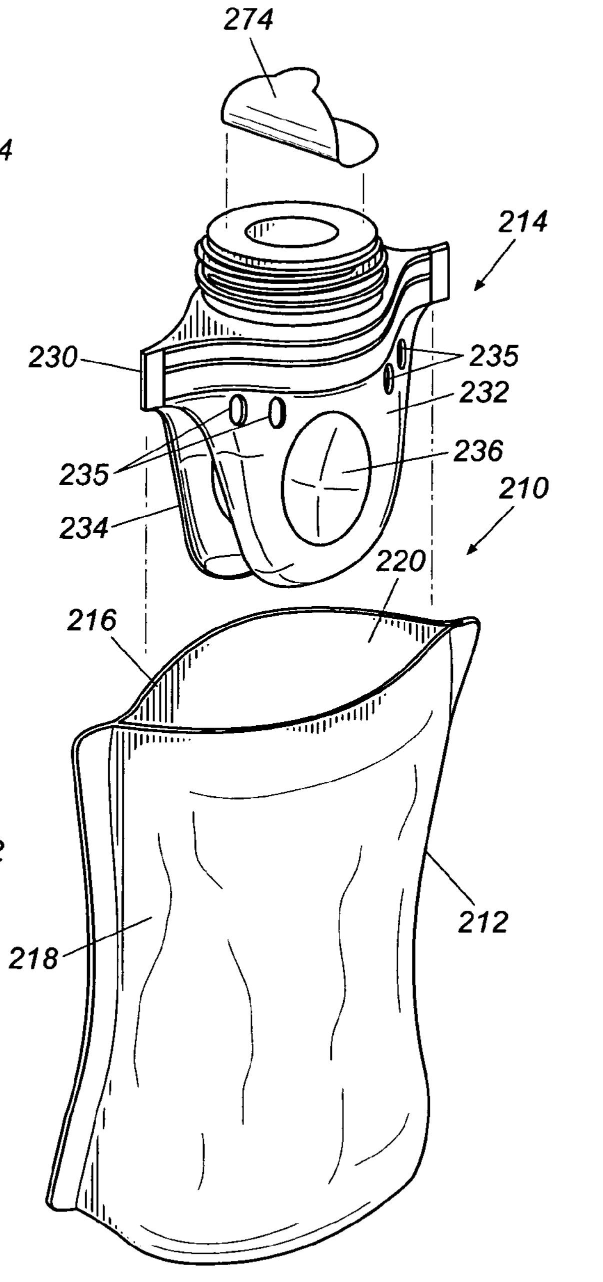
FIG. 5 is an exploded perspective view of an embodiment of an infant feeding pouch of the present invention.

FIG. 5 discloses yet another embodiment where a bottle 210 includes a pouch 212 adapted to receive a fitment 214. Pouch 212 and fitment 214 are formed substantially the same as pouch 12 and fitment 14 above. Pouch 212 has pouch walls 216 and 218 and a base (not shown). Pouch walls 216 and 218 and the base form an interior chamber 220.

Fitment 214 differs from fitments 14 and 114 in that fitment walls 232 and 234 are substantially rounded and do not extend the full length or width of pouch walls 216 and 218. Fitment walls 232 and 234 connect to the bottom of bonding portion 230 and may extend vertically downward or, alternatively, downwardly at a slight outward angle. Each fitment wall 232 and 234 is formed with a plurality of holes 235. Holes 235 allow liquid trapped between fitment walls 232 and 234 and pouch walls 216 and 218, respectively, to flow through and into the main pouch chamber 220 so that substantially all of the liquid in pouch 12 may reach the nipple. A recess 236, which may be formed in fitment walls 232 and 234, enhances the caregiver's grasp on bottle 110 by receiving the caregiver's thumb and forefinger. Similar to bottle 10, a seal 274 may be received on the fitment mouth. Otherwise, all other parts of bottle 210 are, and operate, substantially the same as in bottles 10 and 110.

Any of the above discussed embodiments of the disposable infant formula feeding pouch may contain prepackaged formula. For example, the disposable pouch may contain premixed liquid formula or pre-measured powdered formula to which water may be added. Additionally, the flexible pouch may also be sold empty for use with separately-sold formula or even with breast milk.

While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, those of ordinary skill in this art should understand that the present invention is not limited to these embodiments since modifications can be made. Therefore, it is contemplated that any and all such embodiments are included in the present invention as may fall within the scope and spirit thereof.

What is claimed is:

1. An infant bottle comprising:

a. a flexible pouch comprising
   a first pouch wall;
   a second pouch wall opposed to said first pouch wall; and
   a base wall connected to said first and said second pouch walls, wherein said first and said second pouch walls define an open end opposite said base wall and wherein the inner surfaces of said first, second, and said base wall define a chamber; and b. a fitment comprising,
   a generally canoe-shaped body for bonding said fitment to an inside edge portion of said first and said second pouch walls;
   a first vertical wall connected to said body and extending substantially parallel to a central axis of said body; and
   a second vertical wall connected to said body and extending substantially parallel to said first vertical wall and the central body axis, wherein the widths of said first and second vertical fitment walls are substantially equal to the widths of the inner surfaces of said first and second pouch walls, and said first and second vertical fitment walls are sized and positioned so as to support said opposed flexible pouch walls when said chamber is empty, and
   wherein said open end of said pouch receives said generally canoe shaped fitment body.

2. The infant bottle in claim 1 further comprising a cylindrical top portion adapted to removably receive a closure.

3. The infant bottle in claim 2 further comprising a closure.

4. The infant bottle in claim 3, wherein said cylindrical top portion further comprises:

a. a first helical thread formed on an outer circumference of said cylindrical top portion;
b. a top rim portion; and
c. an annular flange formed on said outer circumference of said cylindrical top portion and located axially below said first helical thread.

5. The infant bottle in claim 4 further comprising an anti-tamper ring.

6. The infant bottle in claim 5, wherein said anti-tamper ring further comprises at least one radially inwardly extending ridge for engaging a bottom surface of said annular flange, and wherein said ring removably secures said closure to said cylindrical top portion.

7. The infant bottle in claim 6 further comprising:

a. an annular cap comprising
   an annular end wall defining an aperture therein;
   a second helical thread formed on an inner circumference of said annular cap; and
b. a nipple that is press-fitable to a bottom surface of said annular end wall and which extends through said annular aperture, wherein said second helical thread is adapted to receive said first helical thread for removably receiving said annular cap onto said cylindrical top portion.

8. The infant bottle in claim 7, wherein said nipple further comprises a radially extending annular flange having an outer radius substantially equal to the inner radius of said annular cap, and wherein said radially extending annular flange is compressible between the bottom surface of said annular end wall and said top rim portion as said annular cap is threadably received by said cylindrical top portion.

9. The infant bottle in claim 6, wherein said closure further comprises:

a. an annular cap, said cap comprising
an annular end wall;
a second helical thread formed on an inner circumference of said annular cap; and an annular disc that is press-fitable to a bottom surface of said annular end wall, wherein the radius of said disc is substantially equal to an inner radius of said annular cap, and wherein an outer edge portion of said disc is compressible between a bottom surface of said annular end wall and said top rim portion as said annular cap is threadably received by said cylindrical top portion.

10. The infant bottle in claim 4, further comprising a safety seal removably attached to said top rim portion.

11. The infant bottle in claim 4, wherein said generally canoe-shaped body is heat bonded to said inside surface of said pouch.

12. The infant bottle in claim 4, wherein said generally canoe-shaped body is ultrasonically bonded to said inside surface of said pouch.

13. The infant bottle in claim 4, wherein said generally canoe-shaped body is adhesively bonded to said inside surface of said pouch.

14. The infant bottle in claim 4, wherein said generally canoe-shaped body is formed from a polymeric material.

15. The infant bottle in claim 3, wherein said pouch contains multiple layers and the inner layer of said flexible pouch is formed from polypropylene.

16. The infant bottle in claim 1, wherein said first and said second vertical fitment walls are spaced apart from each other so that said vertical fitment walls are proximate an interior surface of said first and said second pouch walls.

17. The infant bottle in claim 1, wherein a length of said first and said second vertical fitment walls is substantially equal to a length of said first and said second pouch walls.

18. The infant bottle in claim 1, wherein said flexible pouch is formed from a plurality of layers of material.

19. The infant bottle in claim 18, wherein said plurality of layers comprises a layer formed from a composition chosen from the group consisting of aluminum oxide-coated PET, silica oxide-coated PET and foil.

20. The infant bottle in claim 19, wherein said plurality of layers comprises a second layer formed from polypropylene.

21. The infant bottle in claim 20, wherein said plurality of layers comprises a third layer formed from nylon.

22. The infant bottle in claim 1, wherein infant formula is housed within said chamber of said pouch.

23. The infant bottle in claim 22, wherein the infant formula is in liquid form.

24. The infant bottle in claim 22, wherein the infant formula is in dry form.

25. An infant bottle comprising:

a. a flexible pouch comprising
a first pouch wall;
a second pouch wall; and
a base wall connected to said first and said second pouch walls, wherein said first and said second pouch walls define an open end opposite said base wall and wherein said first, second, and said base wall define a chamber; and b. a fitment comprising,
a generally canoe-shaped body for bonding said fitment to an inside edge portion of said first and said second pouch walls;
a first vertical wall connected to said body and extending substantially parallel to a central axis of said body; and
a second vertical wall connected to said body and extending substantially parallel to said first vertical wall and the central body axis, wherein said open end of said pouch receives said generally canoe shaped fitment body and wherein said first and said second vertical fitment walls define a recessed area on their exterior surfaces.

26. The infant bottle in claim 25, wherein a width of said first and said second vertical fitment walls is substantially equal to a width of said first and said second pouch walls.

27. The infant bottle in claim 25, wherein said first and said second vertical fitment walls define a plurality of holes therethrough.

28. An infant bottle comprising:

a. a flexible pouch comprising,
a closed end,
an open end, opposed side walls and
a defined chamber, b. a fitment, said fitment comprising,
a cylindrical top portion defining a first axial bore therethrough, wherein said cylindrical top portion is adapted to receive a nipple,
a body for bonding said fitment to said open end of said pouch, said body defining a second axial bore formed therethrough, wherein said first and said second axial bores and said pouch chamber are in communication, and
an axially downwardly extending structure comprising fitment walls, sized and positioned so as to support said opposed flexible pouch side walls when said defined chamber is empty, wherein said walls contain a plurality of holes therethrough, wherein said open end of said pouch receives said body, and wherein an inner surface of said pouch is bonded to an outer surface of said body.

29. The infant bottle in claim 28, where said cylindrical top portion further comprises:

a. a first helical thread formed on an outer circumference of said cylindrical top portion;
b. a top rim portion; and
c. an annular flange formed on said outer circumference of said cylindrical top portion and located axially below said first helical thread.

30. The infant bottle in claim 29, comprising an anti-tamper ring.

31. The infant bottle in claim 29, comprising a closure having:

a. An annular cap comprising,
an annular end wall defining an aperture therein,
a second helical thread formed on an inner circumference of said annular cap, and
b. a nipple press-fitable to a bottom surface of said annular end wall and extending through said aperture,
wherein said second thread is adapted to receive said first thread for removably receiving said annular cap onto said cylindrical top portion.

* * * * *

UNITED STATES PATENT AND TRADEMARK OFFICE

CERTIFICATE OF CORRECTION

PATENT NO. : 6,991,121 B1 
DATED : January 31, 2006
INVENTOR(S) : Stuart R. Kipperman, Hagins Fugate and George Nukuto It is certified that error appears in the above-identified patent and that said Letters Patent is hereby corrected as shown below:

Column 3,
Line 26, replace "loose" with -- lose --.
Line 56, remove "," between "continuous" and "walls".

Signed and Sealed this

Thirtieth Day of May, 2006

JON W. DUDAS
*Director of the United States Patent and Trademark Office*